United States Patent
Danley et al.

(10) Patent No.: US 6,523,998 B1
(45) Date of Patent: Feb. 25, 2003

(54) THERMAL ANALYSIS ASSEMBLY WITH DISTRIBUTED RESISTANCE AND INTEGRAL FLANGE FOR MOUNTING VARIOUS COOLING DEVICES

(75) Inventors: Robert L. Danley, Collingswood, NJ (US); John W. Schaefer, Wilmington, DE (US)

(73) Assignee: TA Instruments, Inc., New Castle, DE (US)

(*) Notice: Subject to any disclaimer, the term of this patent is extended or adjusted under 35 U.S.C. 154(b) by 24 days.

(21) Appl. No.: 09/769,320

(22) Filed: Jan. 26, 2001

(51) Int. Cl.[7] .............. G01N 1/00; G01K 1/20; G01K 17/04; G01K 17/08
(52) U.S. Cl. .............. 374/12; 374/32; 374/33; 374/31; 374/10
(58) Field of Search .............. 374/10–12, 29–31, 374/33, 1, 32, 43, 55

(56) References Cited

U.S. PATENT DOCUMENTS

| | | | |
|---|---|---|---|
| 3,339,398 A | 9/1967 | Barrall et al. | |
| 3,456,490 A | 7/1969 | Stone | |
| 3,572,084 A | 3/1971 | May | |
| 3,774,078 A | * 11/1973 | Martin | 317/100 |
| 3,813,937 A | * 6/1974 | Fletcher et al. | 73/190 R |
| 4,031,740 A | 6/1977 | Achermann | |
| 4,979,896 A | 12/1990 | Kinoshita | |
| 5,224,538 A | * 7/1993 | Jacoby | 165/166 |
| 5,224,775 A | 7/1993 | Reading et al. | |
| 5,484,204 A | 1/1996 | Damley | |
| 5,876,118 A | 3/1999 | Vogel | |
| 5,978,216 A | * 11/1999 | Choi | 361/690 |
| 6,238,613 B1 | * 5/2001 | Batchelder et al. | 264/404 |
| 6,308,518 B1 | * 10/2001 | Hunter | 62/3.3 |
| 6,428,203 B1 | * 8/2002 | Danley | 374/10 |
| 2002/0018509 A1 | * 2/2002 | Boiarski | 374/11 |
| 2002/0029567 A1 | * 3/2002 | Kamen et al. | 60/517 |
| 2002/0163781 A1 | * 11/2002 | Bartola et al. | 361/669 |

FOREIGN PATENT DOCUMENTS

| | | |
|---|---|---|
| JP | 10-54813 | 2/1998 |
| JP | 10-132770 | 5/1998 |
| JP | 10246577 A2 | 9/1998 |
| JP | 2000174182 A * | 6/2000 |

OTHER PUBLICATIONS

CA Selects: Thermal Analysis (Issue 10, 1998), p. 27, synopsis of JP–10–54813 [item 9 above].

* cited by examiner

Primary Examiner—Christopher W. Fulton
Assistant Examiner—Gail Verbitsky
(74) Attorney, Agent, or Firm—Shaw Pittman LLP

(57) ABSTRACT

An improved differential thermal analysis/differential scanning calorimetry (collectively, DSC) assembly with a furnace block assembly having a measurement chamber and a furnace heater. The measurement chamber has a sensor assembly for receiving a sample material and a reference material. The furnace block assembly is coupled to a generally cylindrical cooling flange through a distributed thermal resistor that allows a constrained heat flow between the furnace assembly and cooling flange. The thermal resistor can also withstand the mechanical stresses associated with the differential expansion and contraction of the furnace assembly and cooling flange without permanent deformation of the thermal resistor. The cooling flange can be coupled to various cooling devices, permitting operation of the overall DSC instrument in a variety of temperature regimes for a variety of applications.

27 Claims, 4 Drawing Sheets

THERMAL ANALYSIS ASSEMBLY WITH DISTRIBUTED RESISTANCE AND INTEGRAL FLANGE FOR MOUNTING VARIOUS COOLING DEVICES

FIELD OF THE INVENTION

The present invention relates to the field of instrumentation for differential thermal analysis and differential scanning calorimetry.

BACKGROUND OF THE INVENTION

Differential thermal analysis (DTA) generally refers to a calorimetric technique for measuring physical properties of a substance by exposing the substance to different temperature regimes. DTA can be employed to measure parameters associated with phase transitions, glass transitions, polymerization/depolymerization, crystallization, softening, sublimation, dehydration, decomposition, oxidation, cure kinetics and so forth. A differential scanning calorimeter (DSC) measures temperatures and heat flows associated with energy-emitting or energy-absorbing (exothermic and endothermic, respectively) material transitions. DSCs are widely used in academic, government and private facilities for research purposes, as well as for quality control and production purposes.

Hereinafter, reference will be made to DSC, although it is to be understood to encompass DTA as well.

Typical DSC instrumentation includes the following basic components: a heated measurement chamber enclosing a sensor assembly upon which the material to be evaluated (the "sample") may be placed; a furnace heater for heating the measurement chamber; and a cooling device. The cooling device acts as a heat sink for the furnace heater. The cooling device may find application when temperature in the measurement chamber is being increased or decreased.

Typical DSC instrumentation also includes control circuitry for controlling the furnace heater/cooling device so as to conform the temperature in the measurement chamber to the programmed temperature profile. The DSC instrumentation may also include output means, such as a printer or video screen or plotter, to present the results of the measurements. Results can be presented as plots of temperature difference versus absolute temperature or heat flow (e.g., watts per gram) versus absolute temperature.

In traditional DSC analysis, the measurement chamber holds a sample of interest and a reference material, which are to be subjected to a programmed temperature profile. The reference material is typically inert over the profile of interest or otherwise well understood. Typically, DSC analyses generally do not use an actual reference material; rather, the reference pan is left empty.

The sample and the reference material are placed on the DSC sensor assembly, which includes a sample position temperature detector and a reference material position temperature detector. These two temperature detectors are typically configured so that the temperature difference between the sample position and the reference material position can be directly measured. FIG. 1b of Reading, et al., U.S. Pat. No. 5,224,775 (the '775 patent), provides an illustration of a basic DSC device. FIG. 1 of Stone, U.S. Pat. No. 3,456,490 (the '490 patent), illustrates another configuration of a basic DSC device. The '775 and '490 patents are herein incorporated by reference in their entirety.

During operation, the furnace heater and/or cooling device are controlled to follow the programmed temperature profile. The temperature difference ΔT (or heat flow into or out of) between the sample and the reference material is measured as a function of the measured sample temperature. The results, such as sudden excursions in the temperature difference ΔT when the sample changes phase or undergoes a chemical reaction, are studied to better understand the properties and behavior of the sample.

There are other variations of such thermal analysis techniques, such as Pressure Differential Scanning Calorimetry (PDSC), Pressure Differential Thermal Analysis (PDTA), Differential Photocalorimetry (DPC), and Pressure Differential Photocalorimetry (PDPC). The invention described hereafter may be applied to such variations, which are all well known in the art.

As should be readily appreciated, it is a significant challenge to design DSC instrumentation that provides an acceptable combination of attributes, such as the temperature profile range, cooling and heating rates (how fast the measurement chamber can be cooled or heated), accuracy, and precision. The temperature profile can range from the lowest to highest achievable value, e.g., −150° C. to +725° C. for the calorimeter disclosed in the '775 patent or −200° C. to +725° C. for the calorimeter disclosed in U.S. patent application Ser. No. 09/767,903 filed on Jan. 24, 2001, as a continuation-in-part of U.S. patent application Ser. Nos. 09/643,870 and 09/643,869. U.S. patent application Ser. No. 09/767,903 filed on Jan. 24, 2001, is hereby incorporated by reference in its entirety. Prior art DSC devices often entail unsatisfactory tradeoffs between such attributes.

Prior art devices have other drawbacks. For example, it is desirable to keep the temperature of the measurement chamber uniform so that both the sample and the reference material are exposed to the same thermal stimulus. Yet, prior art designs are often susceptible to temperature variations or gradients in the measurement chamber. Such temperature nonuniformities are difficult to predict/measure so as to compensate for them through signal processing. These phenomena can lead to measurement errors.

It has also been difficult to strike an acceptable balance between high cooling rates and temperature uniformity in prior art designs. For example, these designs may permit high cooling rates, but tend to do so at the expense of uniformity.

Finally, prior art designs have not readily lent themselves to a modular configuration that permits easy and rapid replacement of components to tailor the DSC instrumentation to the application. Even where prior art configurations might physically permit modular substitution of components (such as replacing a cooling device of a first type with a cooling device of a second type), the inherent design characteristics of prior art configurations may greatly limit the benefit of such modularity. For example, a DSC unit may permit a "cooling fin" device to be coupled to the measurement chamber/furnace heater to provide a heat sink during above-ambient "hot" measurements. The application is then changed so that substantially below-ambient "cold" measurements are desired. The prior art design may physically permit substituting the cooling fin with a high-powered "liquid cooled heat exchanger." However, the prior art's design characteristics (e.g., very inefficient heat transmission paths) may not permit operation down to the desired low temperature even with the more effective cooling device.

SUMMARY OF THE INVENTION

To overcome these drawbacks or disadvantages in the prior art, and in accordance with the purpose of the invention, as embodied and broadly described, an embodiment of the present invention comprises a DSC coupling assembly for coupling a furnace block assembly (sometimes referred to as a "DSC cell," having a furnace heater for heating a measurement chamber containing a DSC sensor upon which the sample and the reference materials are placed) to a variety of cooling devices. The DSC coupling assembly comprises a distributed thermal resistor attached to a cooling flange.

The distributed thermal resistor has the thermal characteristic of permitting moderate heat flow between a furnace heater and the cooling flange so as to support experiments in a variety of temperature regimes, high and low. The distributed thermal resistor has the mechanical characteristic of being adapted to withstand, without permanent deformation, the mechanical strains associated with the relative movement of the furnace assembly and cooling flange (due to expansion and contraction) during operation.

The cooling flange of the DSC coupling assembly is coupled to the thermal resistor. The cooling flange has the thermal characteristic of moderate conductivity permitting even and efficient heat flow through the thermal resistor. The cooling flange has the mechanical characteristic of having a standard shape profile permitting ready coupling to various cooling devices. In attaching a selected cooling device to the cooling flange, physical contact and thermal paths between the measurement chamber and cooling device are well defined and reproducible.

The advantages of the present DSC coupling assembly are numerous. The distributed, moderate heat flow through the thermal resistor permits the use of various cooling devices to support experiments in a variety of temperature regimes. The structure of the thermal resistor provides a resilient, long-life coupling assembly that will not permanently deform due to operational stresses. The efficient and even heat flow through the cooling flange maximizes temperature uniformity within the measurement chamber, while still achieving the desired high cooling and heating rates. It also permits use of the DSC coupling assembly in a wide variety of temperature regimes. A further advantage is that the configuration of the cooling flange permits attachment of selectable cooling devices in a manner that minimizes undesired heat flow from the measurement chamber.

Accordingly, an object of the invention is to provide a DSC coupling assembly that provides well defined and reproducible heat transfer.

Another object of the invention is to provide a DSC coupling assembly that permits a broad temperature profile range with heating and cooling rates that are more rapid than those achieved in the prior art.

Another object of the invention is to provide a DSC coupling assembly with improved temperature uniformity characteristics.

An object of a preferred embodiment of the invention is to provide a DSC coupling assembly with a generally modular configuration that permits effective operation with a multiplicity of cooling devices that are easily interchanged.

These and other objects of the present invention are described in greater detail in the following description of the invention, the appended drawings, and the attached claims.

DETAILED DESCRIPTION OF THE INVENTION

Figure 1:
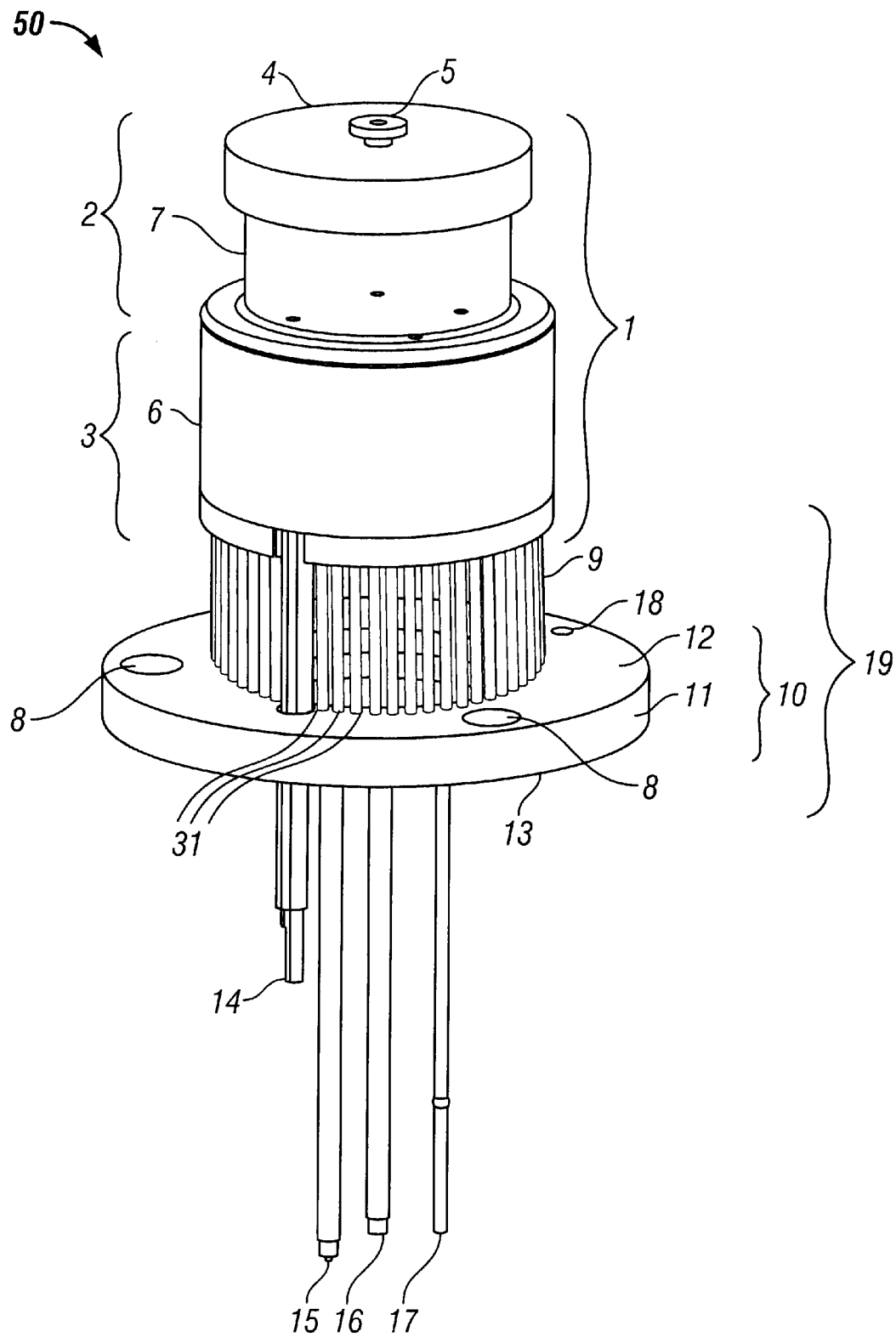
FIG. 1 provides a tilted front view of a preferred embodiment of the present invention.

FIG. 1 provides a perspective front view of an exemplary DSC assembly 50 that can be readily coupled to a variety of cooling devices. DSC assembly 50 includes basic components furnace block assembly 1 and DSC coupling assembly 19. DSC coupling assembly 19 of the present invention permits coupling of furnace block assembly 1 to a variety of cooling devices for effective, efficient measurements in a wide range of temperature regimes. It will be appreciated by those of skill in the art that furnace block assembly 1 is exemplary and illustrative only, and that different furnace block designs could be coupled to DSC coupling assembly 19.

As depicted in FIG. 1, the basic components of DSC assembly 50 are furnace block assembly 1, DSC coupling assembly 19 comprising thermal resistor 9 and cooling flange 10. FIG. 1 also shows leads 14, 15, 16 and purge gas tube 17. DSC assembly 50 of FIG. 1 can be coupled to a selected cooling device at cooling flange 10.

Furnace block assembly 1 encloses DSC sensor 22 (shown in FIG. 2) that receives the sample and the reference material to be measured and provides the thermal stimulation during the course of a measurement. Thermal resistor 9 provides a conduit for heat conduction from furnace block assembly 1 to cooling flange 10 and then to the cooling device (not shown). Cooling flange 10 receives the heat transmitted from furnace block 1 and transmits it to the cooling device, which is coupled to surface 12 of cooling flange 10. Cooling flange 10 also provides a reliable, standard physical interface between DSC assembly 50 and replaceable cooling devices.

Furnace block assembly 1 comprises measurement chamber 2 and furnace heater 3. Measurement chamber 2, which holds the sample and the reference material, includes generally cylindrical main body 7 topped by outer cover 4 that has handle 5. Measurement chamber 2 encloses the sample and the reference material. When activated, furnace heater 3 heats measurement chamber 2 to heat the sample and the reference material (if a reference material is used). When activated, furnace heater 3 heats measurement chamber 2 to heat the sample and the reference material. Generally, cylindrical furnace heater 3 includes a series of electrically resistive windings (not shown) around its circumference, which are then secured with cement 6. Cement 6 can be selected depending on the operating range of the device. For example, for operating at high temperatures, ceramic cements are preferable. When current is applied, these windings will cause furnace heater 3 to provide heat to measurement chamber 2.

As indicated above, furnace block assembly 1 is an exemplary furnace block assembly intended to provide but one example of how a DSC coupling assembly 19 could integrate a given furnace block assembly with a selected cooling device. The artisan of ordinary skill will readily appreciate that other furnace block assemblies could be employed as long as they maintain the characteristic of providing well defined and reproducible heat exchange between the furnace block assembly (or its components) and the cooling device.

Figure 2:
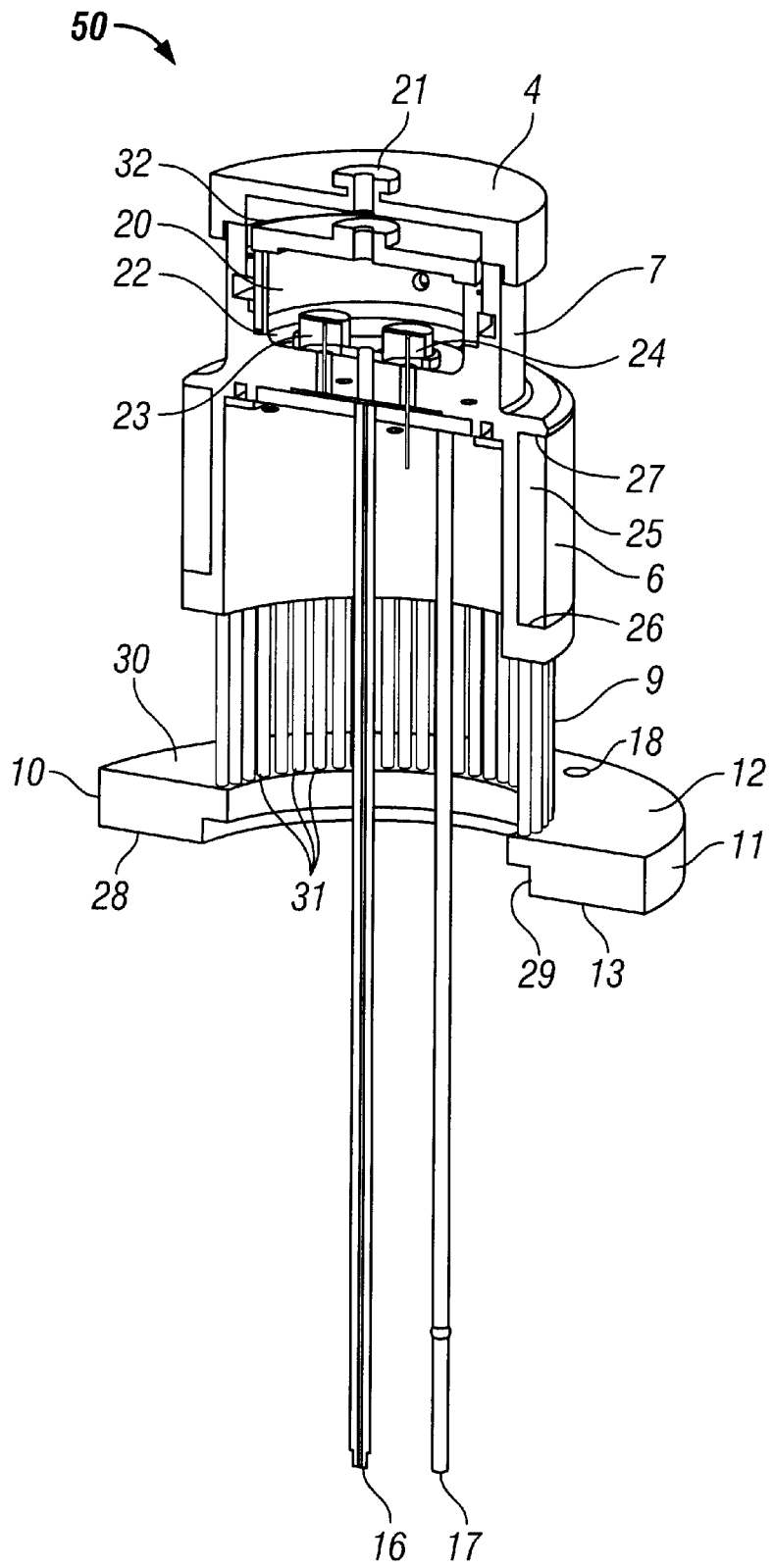
FIG. 2 provides a rotated cutaway view of a preferred embodiment of the present invention.

FIG. 2 provides a cutaway illustration of the assembly of FIG. 1. Inner cover 32 is removed to insert the sample and the reference material. Outer cover 4 further isolates inner cover 32 from the external environment. The sample and the reference material are located in pans placed upon DSC sensor 22 at locations 23 and 24, which include temperature detectors for measuring differential temperature that may be converted into heat flow. Temperature detectors, for example, may be thermocouples. Specific examples of thermocouples include Type E chromel-constantan thermocouples. Other temperature detectors may include platinum resistance thermometers.

Referring to FIG. 2, the windings are applied in a spool-like manner to thin wall cylindrical section 25 between upper flange 27 and lower flange 26. This mechanism for heating is exemplary only and other mechanisms for heating furnace heater 3 could be employed. For example, heating strips or other types of heating elements could be employed instead of windings.

Continuing with FIG. 1, furnace block assembly 1 is preferably an integral body made of a high thermal conductivity material that is resistant to corrosion, such as silver. The integral body and high thermal conductivity provide a uniform temperature distribution across measurement chamber 2. Temperature gradients and other nonuniformities may be harmful to accurate and precise measurements. For example, they may result in the sample and the reference material being exposed to different temperatures. The use of an integral body for furnace block assembly 1 is exemplary only. Two-piece or other constructions could be employed so long as the desired thermal conductivity/uniformity is achieved and the overall furnace block assembly can be reliably coupled to DSC coupling assembly 19.

Thermal resistor 9 provides a well defined thermal path between furnace heater 3 and the cooling flange 10. During high temperature above-ambient testing, thermal resistor 9 provides a pathway to the heat sink via cooling flange 10. Yet it does not place such a cooling load on furnace heater 3 such that it cannot reach desired maximum temperatures or desired heating rates. Additionally, thermal resistor 9 is designed to withstand the mechanical stresses associated with the differential expansion and contraction that furnace heater 3 and cooling flange 10 will undergo during operation. Accordingly, the materials and structure are selected so that thermal resistor 9 can withstand these stresses without breakage or permanent deformation.

Still referring to FIG. 1, according to one embodiment thermal resistor 9 is designed to have a thermal resistance in the range 1 to 5° C./W (degrees Celsius per Watt), preferably about 3° C./W. This value permits DSC coupling assembly 19 to be used with a variety of cooling devices to permit a broad temperature profile range capability in a generally efficient manner. For example, this value is sufficiently high that exemplary furnace block assembly 1 can be adequately cooled using a finned cooling device during above-ambient operations. On the other hand, if below-ambient operations with an alternate cooling device are desired, a value of about 3° C./W is not so high that either the substituted cooling device will be overpowered or furnace 3 will be underpowered (i.e., will not be able to produce enough power to achieve the desired temperature and heating rates) as a result of inadvertent heat transfer from furnace heater 3.

Along with the desired thermal conductivity, thermal resistor 9 should also demonstrate mechanical strength and resilience (flexibility), as well as resistance to oxidation and corrosion. These characteristics extend the operational life of thermal resistor 9.

For example, thermal resistor 9 may be constructed using a nickel alloy, such as nickel alloy 201, which provides an acceptable combination of thermal conductivity, mechanical strength, and resistance to corrosion and oxidation. Other metals and/or metal alloys suitable to the desired temperature range and having appropriate mechanical properties may also be used.

Now turning to the construction of thermal resistor 9, in one embodiment it comprises a series of thin members 31 disposed between the bottom of furnace heater 3 and top of cooling flange 10. The length and thickness of thin members 31 are chosen so that the strains induced by the differential expansion are within the elastic operating range of the material. This makes it less likely that the thin members 31 will be deformed over time through the accumulation of plastic strain.

In one embodiment thin members 31 comprise a series of cylindrical rods having a diameter in the range of about 25 to 75 one-thousandths of an inch (0.025 of an inch to 0.075 of an inch), preferably about 50 one-thousandths of an inch in (0.050) diameter. In this exemplary embodiment the cylindrical rods are in the range of 0.4–1.0 inch in length, preferably about 0.7 inch.

Thin members 31 could alternatively have a rectangular cross-section, triangular cross-section, hexagonal cross-section, or other cross-sectional shape. Generally, manufacturability/cost considerations militate in favor of using the generally circular cross-section.

Selection of particular values for length and diameter (or like dimensions for rectangular, triangular, and other cross-sectional shapes) is a function of both the desired thermal resistance (e.g., 3° C./W) and mechanical resilience (e.g., absence of permanent deformation in the temperature range −200° C. to +725° C. Such design goal parameters can be evaluated by varying the relevant dimensions of thin members 31 using theoretical equations, computer simulations or empirical tests.

Now referring to their arrangement with respect to cooling flange 10 and furnace heater 3, the lengthwise axes of thin members 31 are substantially perpendicular to the top 12 of cooling flange 10 and bottom of furnace heater 3. The upper and lower ends of thin members 31 are coupled to furnace heater 3 and cooling flange 10, respectively, through brazing. Other techniques for attachment could be used.

As illustrated in FIG. 1, the series of thin members 31 comprising thermal resistor 9 are equally spaced to preserve temperature uniformity along an inner circumference or periphery on the top surface 12 of cooling flange 10. Other spacing patterns (such as a rectangular, triangular, hexagonal, etc.) could be used. One benefit of the roughly equidistant spacing is that heat transmitted through thermal resistor 9 is conducted to cooling flange 10 in a relatively uniform manner. This relatively uniform transfer of heat reduces the likelihood of thermal gradients and nonuniformities in measurement chamber 2.

Another benefit of the generally equidistant, cylindrical spacing of thin members 31 as depicted in FIG. 1 is that the resulting overall structure is mechanically robust. The generally cylindrical array defined by thin members 31 is sufficiently flexible to absorb differential expansion strains during measurement operations, and is sufficiently resilient to return to its nominal shape afterwards. Thin members 31 could be alternatively arranged so as to define a generally rectangular, triangular, hexagonal or other array adequate to absorb operational stresses without permanent deformation.

FIG. 2 provides a cutaway view of thermal resistor 9 comprised of thin members 31. Although not depicted in FIGS. 1 or 2, it should be noted that an alternative arrangement for thermal resistor 9 would provide for a contiguous thin-walled cylinder in place of the series of thin members 31. Such a thin-walled cylinder may define an inner circumference on the top surface 12 of cooling flange 10 similar to that defined by the array of thin members illustrated in FIGS. 1 and 2. The wall thickness of such a thin-walled cylinder would be in the range of about 5 to 50 one-thousandths of an inch (0.005 to 0.05 inch) for a cylinder having a diameter of 1 to 1.5 inches. The height of such a thin-walled cylinder would be at the lower end of the 0.4 to 1.0 inch range. Generally, an array of individual members is preferred over a thin-walled cylinder because the former provides a more acceptable combination of stress absorption and resilience.

Returning to FIG. 1, cooling flange 10 physically couples thermal resistor 9 to the cooling device. Because the design of the DSC assembly 50 of FIG. 1 supports a broad range of applications (high temperature profiles, low temperature profiles, fast heating and cooling rates, etc.), the operator can attach a variety of cooling devices to cooling flange 10 based on the requirements of the application. A nonexhaustive list of cooling devices that could be connected to cooling flange 10 includes: cooling fins (natural or forced convection), liquid cooled heat exchangers, gas cooled heat exchangers, and change of phase liquid-gas heat exchangers (open loop or closed loop). Other types of cooling devices could also be used.

In one embodiment, cooling flange 10 is a generally cylindrical disk having a top surface 12, a bottom surface 13, and a lateral surface 11 defining an outer circumference. Cooling flange 10 is adapted to interface with a cooling device having an opening at one end which is generally reciprocal to top surface 12 and lateral surface 11. While not illustrated by FIG. 1, such cooling devices will typically have a cylindrical shape with an opening that allows them to be slid over furnace block assembly 1. The opening then reciprocally mates with lateral surface 11 (to hold the cooling device in place) and with top surface 12 (for heat transfer and to provide vertical support). Accordingly, the heat transfer from cooling flange 10 to the cooling device will be fairly uniform with the dominant heat transfer mechanism being from top surface 12 (rather from lateral surface 11) to the cooling device.

There are several other details of cooling flange 10 that may vary according to the particular embodiment without departing from the spirit and scope of the invention. In FIG. 1, there are support holes 8 in cooling flange 10 for holding supporting leg members (not shown) supporting an entire structure. These supporting leg members, which extend down to a base support, are preferably tubes or rods with a low thermal conductivity, such as stainless steel. This low thermal conductivity of the leg members minimizes any heat flow through the legs to cooling flange 10. FIG. 1 also depicts mounting hole 18 for attaching a temperature detector to surface 13 to monitor the temperature of cooling flange 10.

Cooling flange 10 is designed to thermally couple furnace heater 3 (a heat producer) to the cooling device (a heat sink). As such, cooling flange 10 should have a high thermal conductivity and should be resistant to moderately high and low temperatures. It should also be resistant to oxidation or corrosion that might impair its heat exchange function. It has been found that cooling flange 10 can be constructed of a nickel alloy, such as nickel alloy 201, which provides a good compromise between the aforementioned considerations. Exemplary dimensions for cooling flange 10 include a diameter along top surface 12 of about 2.37 inches and a width of about 0.375 inches along lateral surface 11.

Figure 3:
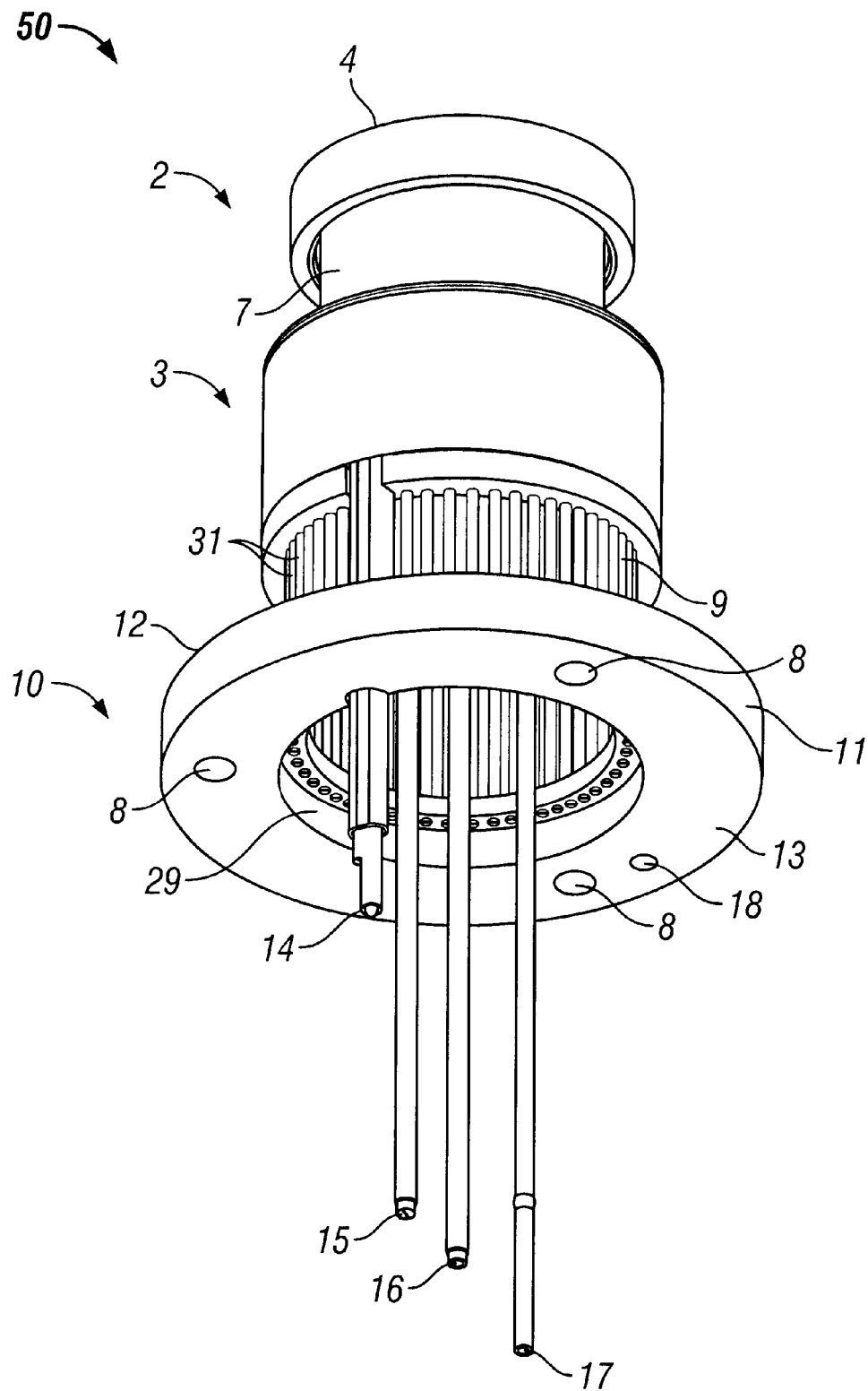
FIG. 3 provides a tilted bottom view of a preferred embodiment of the present invention.

A cutaway view of cooling flange 10 is provided in FIG. 2. In this embodiment, bottom surface 13 has been countersunk to a depth 29. In this embodiment, the diameter of the countersink hole in bottom surface 13 is somewhat larger than the hole in the top surface 12 around which thin members 31 are arranged. Accordingly, distance 28 is somewhat smaller than distance 30. As shown in FIG. 3, this permits the lower end of thin members 31 to terminate at the top of depth 29. In this embodiment, the difference in the diameters of the hole in bottom surface 13 and that in top surface 12 is greater than the diameter of thin members 31.

As depicted in the exemplary embodiment of DSC assembly 50 in FIG. 1 and FIG. 3, leads 14, 15, 16 project from the bottom of that assembly. In one embodiment, lead 14 is the heater lead for providing power to the heater coils of furnace heater 3. Lead 15 connects to an overtemperature sensor located in furnace block assembly 1. Lead 16 connects to the thermocouple sensors in measurement chamber 2. Finally, purge gas tube 17 discharges gas into measurement chamber 20.

Figure 4:
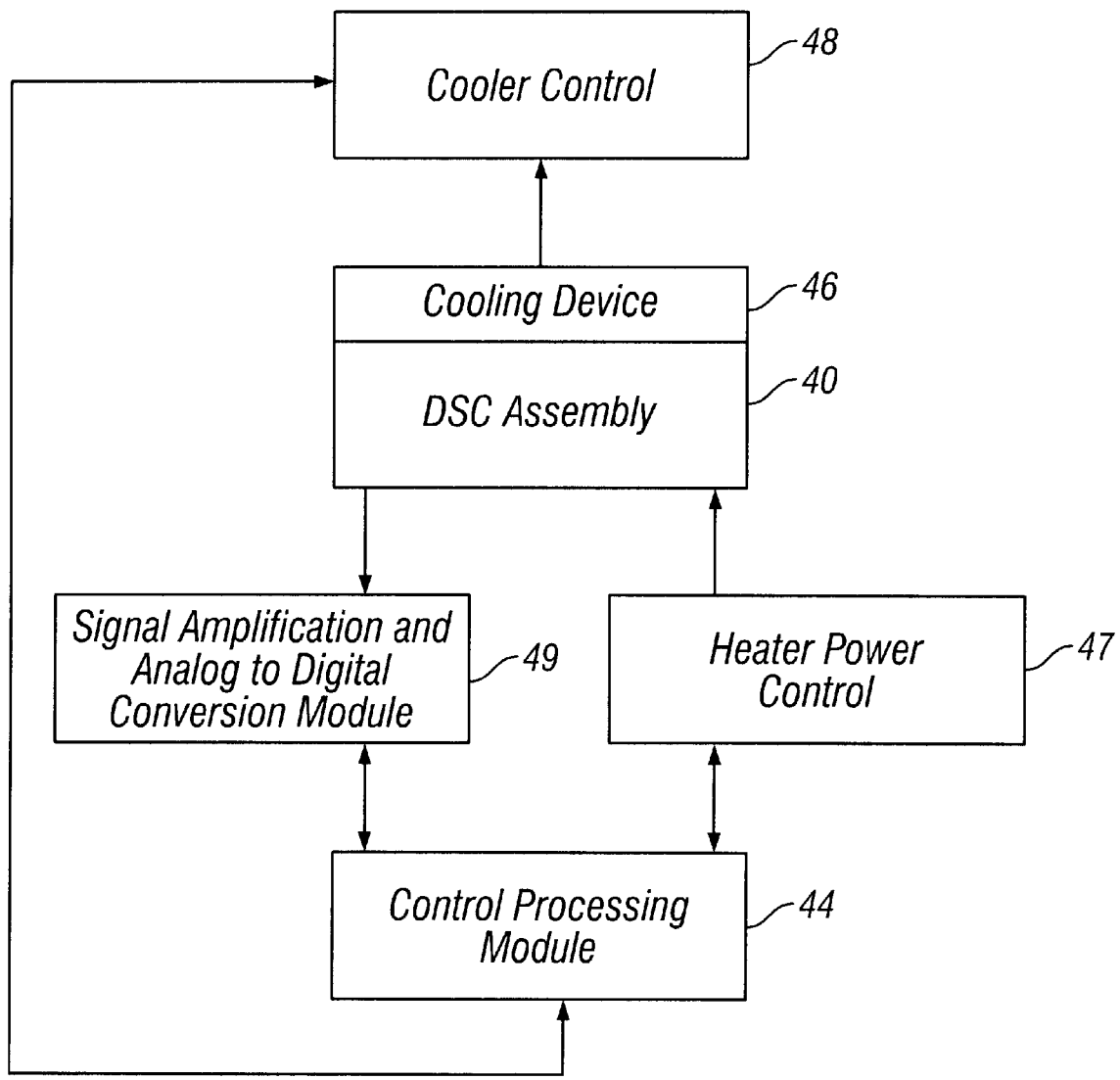
FIG. 4 is a functional block diagram illustrating the operational environment of the preferred embodiment of the present invention.

FIG. 4 provides a functional block diagram illustration of the operational environment of the present invention. DSC assembly 40 is similar to that previously described as DSC assembly 50 in FIG. 1, which is coupled to replaceable cooling device 46 that is suitable for the desired application. As previously mentioned, cooling device 46 might comprise a cooling fin type device, liquid cooled heat exchanger, gas cooled heat exchanger, change of phase heat exchanger, and so on. Once DSC assembly 40 is integrated with cooling device 46, heater power control 47 is provided for heater power, and cooler controller 48 enables cooling device 46. Of course, there may be no control requirements for replaceable cooling device 46, if cooling device 46 is, for example, a cooling finned natural convection device.

Control processing module 44 includes the control processing circuitry for ensuring that DSC assembly 40 follows the temperature profile input. Control processing module 44 receives measurements of heat/temperature from the signal amplifier and analog to digital conversion module 49 and adjusts heater power control 47 to follow the programmed temperature profile. In theory, control processing module 44 could request that the cooler controller 48 change the cooling load as part of the temperature control process. However, it is been found that it is generally more efficient for heater power to be the sole output control parameter and, accordingly, cooler controller 48 is preferably not adjusted by control processing module 44. Temperature sensor outputs from DSC assembly 40 are amplified and converted into a digital format by signal amplification and analog to digital conversion module 49 and are read by control processing module 44 (which may further process the measurements and format them for output as graphs or the like on a computer video screen, a plotter, or a hard copy printer).

The artisan of ordinary skill will readily recognize that the block diagram of FIG. 4 is a functional representation and that certain functions could be combined or further subdivided. For example, the operations of control processing module 44, heater power control 47 and signal amplification and analog to digital conversion module 49 could easily be performed on a single programmable or special application computer.

Having described an improved DSC assembly using a distributed thin member thermal resistor coupled to a generally cylindrical cooling flange, it should be apparent to the artisan of ordinary skill that numerous advantages flow from this configuration. The design is robust insofar as its heat flow characteristics and shape permit a multitude of cooling devices to be employed. The user simply swaps one cooling device for another according to the requirements of a particular test.

Another advantage is that the distributed thermal resistor provides uniform and reproducible cooling for accurate, precise measurements. Moreover, the physical configuration of the thermal resistor is robust, tolerating simultaneous expansion of the heater and contraction of the cooling flange. Yet the thermal resistor is resilient and returns to its nominal shape after such mechanical stresses.

The location of the thermal heater between the measurement chamber and the cooling device in the present invention is a further advantage. In this orientation, heat flowing towards the heat sink (cooling flange/cooling device) avoids the measurement chamber and thus the problem of temperature nonuniformity is greatly mitigated.

In sum, the overall robustness of the design facilitates DSC measurement with a broad thermal profile, high heating and cooling rates, low noise and moderate power consumption. Other advantages and benefits exist.

Embodiments of systems and methods have been described. In the foregoing description, for purposes of explanation, numerous specific details are set forth to provide a thorough understanding of the present invention. It will be appreciated, however, by one skilled in the art that the present invention may be practiced without these specific details. Additionally, in the foregoing detailed description, the present invention has been described with reference to specific exemplary embodiments. These specific embodiments are intended to be exemplary only and, accordingly, the present specification and figures are to be regarded as illustrative rather than restrictive.

What is claimed is:

1. A differential scanning calorimeter comprising:
   a measurement chamber for receiving a sample;
   a furnace heater operatively coupled to the measurement chamber for heating the measurement chamber;
   a cooling flange operating as a heat sink with respect to the measurement chamber; and
   a thermal resistor having a series of longitudinal members,
   wherein the cooling flange comprises a generally cylindrical disk having a generally flat top surface, a bottom surface, and a lateral surface defining an outer circumference, and further wherein the series of longitudinal members are disposed at a substantially perpendicular angle to said top surface and define a generally circular pattern along an inner periphery of the cooling flange,
   wherein the thermal resistor provides a well defined heat conduction path from the furnace heater to the cooling flange.

2. The calorimeter of claim 1, wherein the longitudinal members are generally cylindrical rods.

3. The calorimeter of claim 1, wherein the longitudinal members comprise rods with a cross section having one of rectangular, hexagonal and triangular shapes.

4. The calorimeter of claim 1, wherein the longitudinal members have a diameter in the range of about 0.025 to about 0.075 inch.

5. The calorimeter of claim 1, wherein the longitudinal members have a diameter of about 0.05 inches.

6. The calorimeter of claim 1, wherein the longitudinal members have a length in the range of about 0.4 to about 1 inch.

7. The calorimeter of claim 1, wherein the longitudinal members have a length of about 0.7 inch.

8. The calorimeter of claim 1, wherein the thermal resistor is constructed of a nickel alloy.

9. The calorimeter of claim 1, wherein the thermal resistor having a thermal resistance ranging from about 1 to about 5° C./W disposed between the furnace heater and the cooling flange for providing a heat transfer path from the furnace heater to the cooling flange.

10. A differential scanning calorimeter comprising:
    a measurement chamber for receiving a sample;
    a furnace heater operatively coupled to the measurement chamber for heating the measurement chamber;
    a cooling flange operating as a heat sink with respect to the measurement chamber; and
    a thermal resistor having a series of longitudinal members,
    wherein the longitudinal members have upper ends and lower ends, and wherein the cooling flange has a generally flat top surface, and wherein the lower ends of the longitudinal members are spaced on the generally flat top surface of the cooling flange such that the distance between each pair of adjacent longitudinal members is approximately the same,
    wherein the thermal resistor provides a well defined heat conduction path from the furnace heater to the cooling flange.

11. The calorimeter of claim 1, wherein each of the longitudinal members has an upper end and a lower end, wherein the lower end terminates at the generally flat top surface of the cooling flange.

12. The calorimeter of claim 1, wherein the furnace heater is disposed between the measurement chamber and the thermal resistor.

13. A differential scanning calorimeter comprising:
    a measurement chamber for receiving a sample;
    a furnace heater operatively coupled to the measurement chamber for heating the measurement chamber;
    a cooling flange operating as a heat sink with respect to the measurement chamber; and
    a thermal resistor having a series of longitudinal members of a nominal shape,
    wherein the thermal resistor provides a well defined heat conduction path from the furnace heater to the cooling flange,
    wherein the thermal resistor experiences differential expansion strains during measurements operations, and
    wherein the thermal resistor returns to the nominal shape upon return to ambient conditions.

14. A differential scanning calorimeter comprising:
    a measurement chamber for receiving a sample;
    a furnace for heating the measurement chamber; and
    a thermal resistor disposed between the furnace and a cooling flange, wherein the thermal resistor comprises a series of longitudinal members,
    wherein the cooling flange comprises a generally cylindrical disk having a generally flat top surface, a bottom surface, and a lateral surface defining an outer circumference, and further wherein the series of longitudinal members are disposed at a substantially perpendicular angle to said top surface and define a generally circular pattern along an inner periphery of the cooling flange, wherein the thermal resistor provides a uniform and well defined heat transfer path from the furnace to the cooling flange.

15. The calorimeter of claim 14, wherein the longitudinal members have a circular cross section.

16. The calorimeter of claim 14, wherein the longitudinal members have a rectangular cross-section.

17. The calorimeter of claim 14, wherein the thermal resistor has a thermal conductivity ranging from about 0.2 to about 1 W/° C.

18. The calorimeter of claim 14, wherein the longitudinal members have upper ends and lower ends, and wherein the cooling flange has a generally flat top surface, and wherein the lower ends of the longitudinal members are spaced on the generally flat top surface of the cooling flange such that the distance between each pair of adjacent longitudinal members is approximately the same.

19. An attachment for coupling a furnace assembly to a cooling device, the furnace assembly including a measurement chamber and a furnace heater, the attachment comprising a thermal resistor comprising a series of longitudinal members having a nominal shape and a flange adapted to be connected to the furnace assembly for transferring heat to the cooling device, wherein the flange comprises means for coupling said the attachment to the cooling device, wherein the thermal resistor experiences differential expansion strains during measurement operations and returns to the nominal shape upon return to ambient conditions.

20. The attachment of claim 19, wherein each of the longitudinal members have an upper end and a lower end, and wherein the flange comprises a generally cylindrical disk having a top surface, a bottom surface, and a lateral surface defining an outer circumference, and wherein the lower ends of the longitudinal members couple to the cylindrical disk at the top surface.

21. The attachment of claim 20, wherein the lower ends attach to the top surface of the cylindrical disk so as to define an inner circumference along the top surface.

22. The attachment of claim 19, wherein the thermal resistor has a thermal conductivity of about 0.2 to about 1 W/° C.

23. The attachment of claim 19, wherein the thermal resistor is a contiguous thin-walled cylinder.

24. The attachment of claim 23, wherein the thin-walled cylinder defines an inner circumference on the top surface of the flange.

25. The attachment of claim 19, wherein the longitudinal members have upper ends and lower ends, and wherein the flange has a generally flat top surface, and wherein the lower ends of the longitudinal members are spaced on the generally flat top surface of the flange such that the distance between each pair of adjacent longitudinal members is approximately the same.

26. An attachment for coupling a furnace assembly to a cooling device, the furnace assembly including a measurement chamber and a furnace heater, the attachment comprising a thermal resistor comprising a series of longitudinal members and a flange adapted to be connected to the furnace assembly for transferring heat to the cooling device, wherein the flange comprises means for coupling said the attachment to the cooling device, wherein the flange comprises a generally cylindrical disk having a generally flat top surface, a bottom surface, and a lateral surface defining an outer circumference, and further wherein the series of longitudinal members are disposed at a substantially perpendicular angle to said top surface and define a generally circular pattern along an inner periphery of the flange.

27. An attachment for coupling a furnace assembly to a cooling device, the furnace assembly including a measurement chamber and a furnace heater, the attachment comprising a thermal resistor comprising a series of longitudinal members and a flange adapted to be connected to the furnace assembly for transferring heat to the cooling device, wherein the flange comprises means for coupling said the attachment to the cooling device, wherein the longitudinal members have upper ends and lower ends, and wherein the flange has a generally flat top surface, and wherein the lower ends of the longitudinal members are spaced on the generally flat top surface of the cooling flange such that the distance between each pair of adjacent longitudinal members is approximately the same.

* * * * *